United States Patent [19]

Truax et al.

[11] Patent Number: 5,242,304
[45] Date of Patent: *Sep. 7, 1993

[54] DENTAL APPLIANCE INCLUDING SURFACE-MOUNTED UNDERCUTS AND METHOD OF MANUFACTURE

[75] Inventors: Lloyd H. Truax; Kevin L. Truax, both of Rochester, Minn.

[73] Assignee: Tru-Tain, Inc., Rochester, Minn.

[*] Notice: The portion of the term of this patent subsequent to Jan. 5, 2010 has been disclaimed.

[21] Appl. No.: 858,607

[22] Filed: Mar. 27, 1992

Related U.S. Application Data

[63] Continuation-in-part of Ser. No. 782,159, Oct. 24, 1991, Pat. No. 5,176,517.

[51] Int. Cl.5 .............................................. A61C 13/12
[52] U.S. Cl. ........................................ 433/177; 433/7; 433/181
[58] Field of Search ................. 433/3, 6, 7, 9, 18, 433/180, 181, 215, 218, 226, 177

[56] References Cited

U.S. PATENT DOCUMENTS

| Re. 15,265 | 1/1922  | Roach      | 433/40  |
|------------|---------|------------|---------|
| 1,367,477  | 2/1921  | Homer      | 433/218 |
| 1,410,311  | 3/1922  | Howe       | 433/40  |
| 2,609,605  | 9/1952  | Dillon     | 433/177 |
| 2,889,625  | 6/1959  | Saffir     | 433/180 |
| 3,357,104  | 12/1967 | Greene et al. | 433/40 |
| 3,521,355  | 7/1970  | Pearlman   | 433/3   |
| 3,745,653  | 7/1973  | Cohl       | 433/24  |
| 3,792,529  | 2/1974  | Goshgarian | 433/7   |
| 3,835,538  | 9/1974  | Northcutt  | 433/24  |
| 4,259,073  | 3/1981  | Emmons     | 433/177 |
| 4,398,887  | 8/1983  | Balde et al. | 433/218 |
| 4,445,861  | 5/1984  | Klepacki   | 433/181 |
| 4,449,928  | 5/1984  | von Weissenfluh | 433/40 |
| 4,768,957  | 9/1988  | Segura     | 433/181 |
| 4,773,857  | 9/1988  | Herrin     | 433/9   |
| 4,834,654  | 5/1989  | Nussbaum   | 433/141 |
| 4,881,898  | 11/1989 | Harvey, Sr. et al. | 433/215 |
| 4,971,558  | 11/1990 | Jacobi     | 433/226 |
| 5,040,981  | 8/1991  | Oliva      | 433/215 |
| 5,055,039  | 10/1991 | Abbatte et al. | 433/6 |
| 5,163,839  | 11/1992 | Metcalf    | 433/6   |

Primary Examiner—John J. Wilson
Attorney, Agent, or Firm—Merchant, Gould, Smith, Edell, Welter & Schmidt

[57] ABSTRACT

A functional dental appliance system and a method of manufacturing the same. At least one surface mounted undercut is attached to the outer surface of the tooth. The dental appliance is constructed of a semi-rigid material which has a shape generally conforming to a portion of the contour of the tooth and the attached undercut. The semi-rigid material permits the dental appliance to deform temporarily prior to engagement with the portion of the tooth and the attached undercut such that the dental appliance returns to an undeformed state when engaged with the tooth and the attached undercut to form a pressure fit engagement relationship. The dental appliance may be manufactured by attaching a surface mounted dental undercut to the outer surface of a tooth and forming the dental appliance to conform to a portion of the outer surface of the tooth and the attached undercut.

22 Claims, 6 Drawing Sheets

DENTAL APPLIANCE INCLUDING SURFACE-MOUNTED UNDERCUTS AND METHOD OF MANUFACTURE

This is a continuation-in-part of application Ser. No. 07/782,159, filed on Oct. 24, 1991, now U.S. Pat. No. 5,176,517.

FIELD OF THE INVENTION

The present invention relates to a functional dental appliance system and a method of manufacturing the same. In particular, a dental appliance is formed to cooperatively engage with the outer surface of a tooth in a patient's mouth and one or more surface-mounted dental undercuts attached to the tooth. The dental appliance is manufactured by attaching at least one surface mounted dental undercut to the outer surface of a tooth and forming the dental appliance to conform to a portion of the outer surface of the tooth and the attached undercut.

BACKGROUND OF THE INVENTION

Dental appliances or prostheses, such as removable orthodontic devices or partial dentures, are typically held in place by securing the appliance to adjacent teeth. An Adam's, ring or "C" clasp is commonly used for this purpose. The clasp is a wire structure which wraps around adjacent teeth, generally along the gum line, in order to provide stable and reliable attachment of the dental appliance.

However, this configuration does not reliably secure a removable dental appliance and can irritate the gum tissue. Further, healthy teeth tend to decay due to contact with the metal clasps and because of the mechanical forces transmitted by the appliance to the health teeth.

In certain circumstances, the crown of a tooth is prepared whereby a portion of the crown is removed and a dental crown is place on the tooth to provide an undercut surface. This method, however, is destructive to the tooth and expensive. For example, U.S. Pat. No. 4,445,861 issued to Klepacki on May 1, 1984 discloses a denture support system where the canine teeth are modified by creating a substantially horizontal ledge, from 0.50 to 0.75 mm wide.

Alternatively, U.S. Pat. No. 4,768,957 issued to Segura on Sep. 6, 1988, discloses a two-part metal coupling system for retaining dentures. The male portion 5 of the couple is glued to an inside face of an anchor tooth. The denture is attached to a female portion 6, which in turn engages directly with the male portion 5. However, the metal coupling system of Segura is more costly to manufacture and the cast metal tab 4 secured to the tooth 1 may cause decay of an otherwise healthy tooth, as discussed above. Further, the metal coupling system and associated dental appliance are significantly larger than the dental appliance system of the present invention.

The present invention addresses these and other problems associated with the prior art.

SUMMARY OF THE INVENTION

The present invention relates to a system for attaching functional dental appliances formed to cooperatively engage with a portion of the outer surface of a tooth in a patient's mouth and one or more surface-mounted dental undercuts attached to the tooth.

More specifically, the present invention is directed to a functional dental appliance with engagement surfaces which create a pressure-fit engagement with the undercut and a portion of the surface of the tooth.

At least one surface mounted undercut is attached to the outer surface of the tooth, so that the undercut extends outwardly from the outer surface of the tooth. The dental appliance is constructed of a semi-rigid resilient material which generally retains its shape. The appliance defines a shape generally conforming with a portion of the contour of the tooth and the outward extension of the attached undercut. The semi-rigid resilient material has sufficient elasticity to permit the dental appliance to deform prior to engagement with the tooth and the attached undercut, such that a portion of the dental appliance can be slightly deformed and then returned to an undeformed state when engaged with the tooth and the attached undercut in a pressure fit engagement relationship.

Alternatively, the pressure-fit engagement may be created between the engagement surfaces of the appliance and the outer surfaces of two or more generally opposing teeth and the undercuts attached thereto.

The method for constructing the functional dental appliance involves attaching at least one surface mounted undercut to the outer surface of the tooth. The dental appliance is created from a semi-rigid, resilient material which has a shape that generally conforms to the attached undercut and a portion of the contour of the tooth.

The functional dental appliance of the present invention may also be manufactured by creating an overlay for a portion of the outer surface of the tooth proximate the attached undercut. The overlay is then used to create a casting or model of a portion of the patient's mouth, from which the dental appliance is formed. Alternatively, the dental undercuts may be attached to the model prior to creation of the appliance. Additional undercuts must then be attached to the patient's teeth at the same location where the undercuts were attached to the model.

Removably securing the functional dental appliance within a patient's mouth, where the patient's mouth includes at least one tooth containing a surface mounted undercut, comprises sliding the appliance over the surface mounted undercut so that the engagement surfaces on the appliance cooperatively engage with the undercut and a portion of the outer surface of the tooth.

As used in the present specification, the term "outer surface", when used in reference to a tooth, may refer to any surface of the tooth which is accessible for purposes of attaching an undercut thereto, including without limit the buccal, lingual, distal or mesial surfaces of the tooth. Outer surface may also be used to refer to a surface of a tooth which has not otherwise been altered to receive an undercut or a dental appliance, but which may have naturally occurring imperfections or other defects in the surface of a tooth. It should also be understood that the surface mounted undercuts of the present invention may be removed when the dental appliance is no longer required, returning the surface of the tooth to its original condition.

Used in the specification, the term "functional dental appliance" refers to any dental appliance, including without limit; binators, Hawley retainers, Clark twin blocks, sagittal appliances, transverse appliances, biofinisher, T.M.J. splints, full dentures, and partial dentures.

The above described features and advantages, along with the various other advantages and features of novelty are pointed out with particularity in the claims of the present invention. However, for a better understanding of the present invention, its advantages, and objects obtained by its use, reference should be made to the drawings which form a further part of the present invention, and to the accompanying descriptive material in which preferred embodiments of the present invention are illustrated and described.

BRIEF DESCRIPTION OF THE DRAWINGS

In the drawings, in which like and primed reference numerals indicated corresponding parts of the respective embodiments throughout the several views.

DETAILED DESCRIPTION OF THE PREFERRED EMBODIMENT

Attachment of the Surface Mounted Dental Undercut

Figure 1:
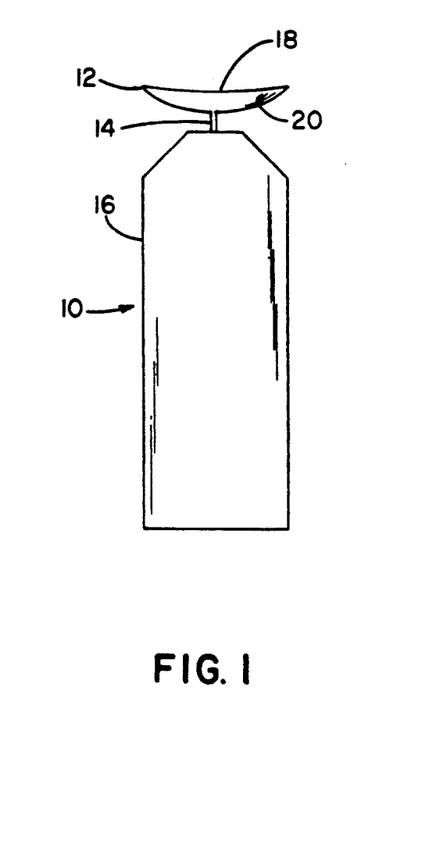
FIG. 1 is a top view of the preferred surface mounted dental undercut application device.

FIG. 1 illustrates the surface mounted dental undercut application device 10 of the preferred embodiment of the present invention. The surface mounted undercut or applique 12 is attached to the tab 16 by an elongated stem 14. In the preferred embodiment of the present invention the undercut application device 10 is formed of a single homogeneous piece of plastic produced through an injection molding process. Lexan TM, an FDA-approved polycarbonate plastic made by General Electric Corporation, is suitable for this purpose. However, it will be recognized by those skilled in the art that the surface mounted dental undercut application device 10 of the present invention could be formed from a variety of materials such as FDA-approved ceramics or metals. Further, the tab 16 and stem 14 portion of the dental undercut application device 10 do not necessarily need to be made from the same material. For example, a ceramic undercut could be connected to a plastic stem and tab with a suitable adhesive.

The front side 18 of the undercut 12 is generally concave in shape, to match the contour of the tooth surface. Likewise, the back side 20 of the undercut 12 may be curved so that the undercut 12 will be properly contoured with the surface of the tooth.

Figure 2:
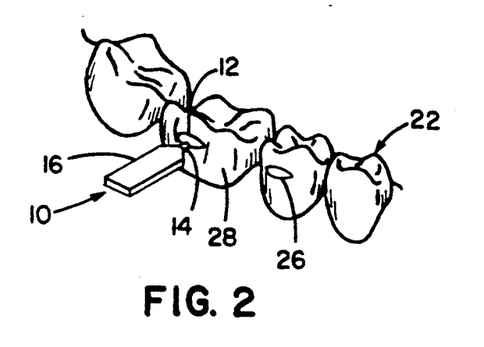
FIG. 2 is a perspective of a patient's mouth showing the preferred surface mounted dental undercut application device for applying the applique or undercut to the outer surface of a tooth.

FIG. 2 is a perspective view of several teeth 22 to which a first undercut or applique 12 is being applied to the surface of the tooth 28 with a suitable adhesive (not shown). FIG. 2 also illustrates a second undercut 26 which has been previously applied. Although FIG. 2 illustrates use of the dental undercut application device 10 of the present invention on the buccal or front view of the teeth, it will be understood by those skilled in the art that the dental undercut application device 10 of the present invention may be applied to any surface of the tooth, including the occlusal or labial surfaces.

The preferred attachment method of the present invention requires that the surface of the tooth 28 be cleaned with a suitable polish or abrasive prior to attaching the undercut 12 of the present invention. The tooth surface 28 is then acid etched in order to create a good bonding surface for the adhesive (not shown). Reliance Gel Etching Agent from Reliance Corporation ® is suitable for this purpose. The etching gel is 50 percent phosphoric acid. The etching gel is applied to the tooth for approximately 60 seconds. The tooth surface 28 is then rinsed with sufficient water to neutralize the etching agent and allowed to dry. A plastic conditioner may be placed on the front side 18 of the undercut 12 and the tooth surface 28 prior to application of the adhesive.

Because the undercut 12 is extremely small, the operator preferably grasps the tab 16 with a hemostat while applying the adhesive to the front side 18 of the undercut 12. The operator may also grasp the tab 16 in his or her fingers. While still holding the tab 16, the operator places the undercut 12 against the surface of the tooth 28. Typically, the undercut 12 is located in approximately the middle or cervical one third of the buccal or labial surface of the tooth. One adhesive suitable for this purpose is made from diacrylate resins available from Reliance Corporation. The adhesive cures when exposed to electromagnetic energy. The Visilux TM light cure unit from Minnesota Mining & Manufacturing of St. Paul, Minn. is suitable for curing the adhesive.

The adhesive cures in approximately 60 seconds. After the operator has determined that the undercut 12 is securely anchored to the surface of the tooth 28, the stem 14 is cut using a ligature wire cutter and the back side 20 of the undercut 12 is smoothed with a diamond stone or sandpaper disk. Because the undercut 12 is extremely small and its contour is smoothed to match the surface of the tooth, the undercut 12 does not significantly reduce the aesthetics of the tooth.

The Removable Functional Dental Appliance System

Figure 3:
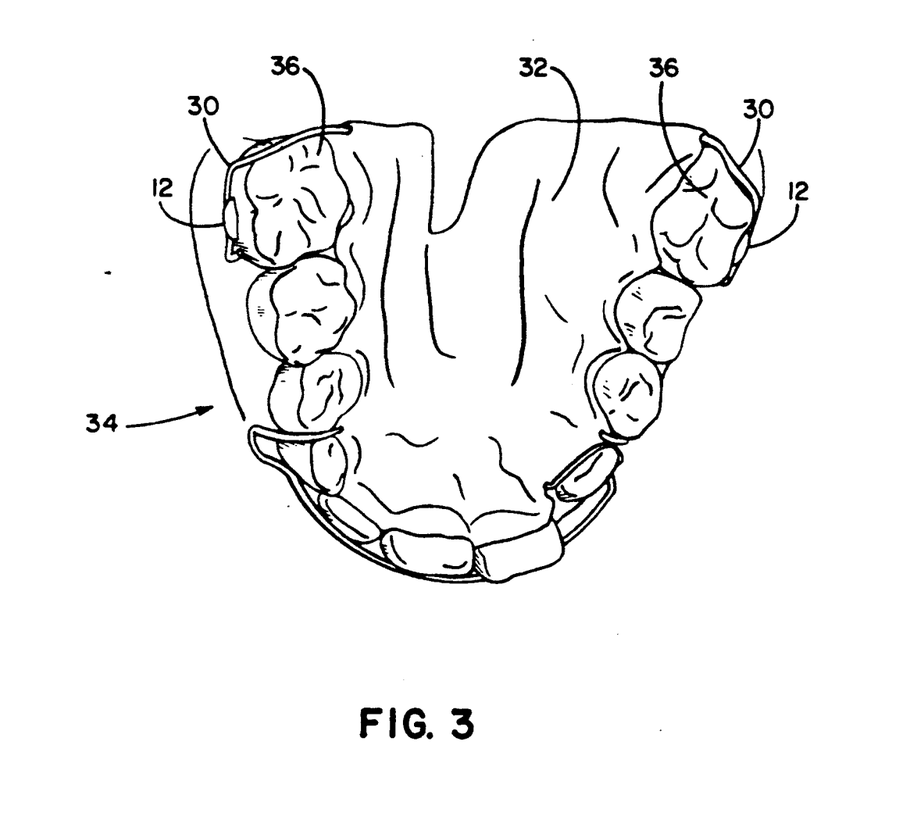
FIG. 3 is a perspective view illustrating the operation of the preferred surface mounted undercut retaining a dental appliance having wire clasps.

FIG. 3 illustrates a perspective view of a dental appliance 32 anchored to mouth section 34 with a series of wire clasps 30. The clasps 30 are formed to engage with the undercuts 12 previously attached to the surface of the teeth 36. Because the clasps 30 do not need to be as accurately fitted around the contour of the teeth 36, the dental appliance 32 is much less expensive to manufacture and can be more easily fitted to the individual patient. Further, the clasps 30 do not need to wrap around the teeth 36 along the gum line. Rather, the clasps 30 only extent around two sides of the teeth 36 and engage the undercut 12 on the surface of the teeth 36 above the gum line, providing greater comfort to the patient and better retention of the removable appliance.

Figure 5:
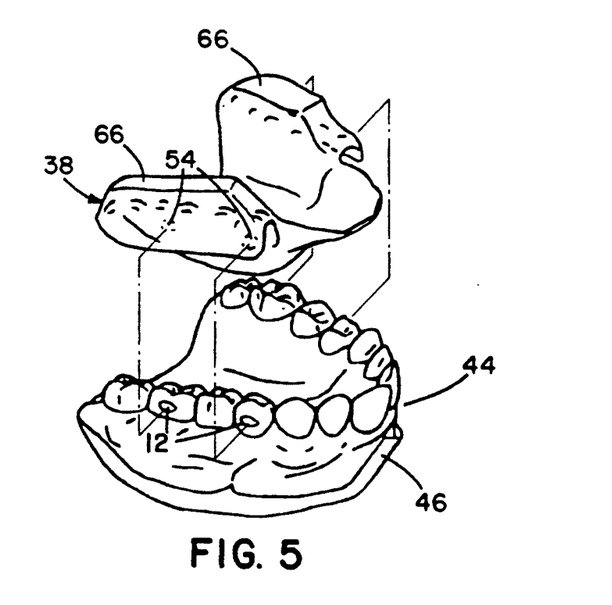
FIG. 5 is an exploded view of the preferred appliance after being formed on a model of the patient's mouth.

The preferred functional dental appliance 38 of the present invention, as illustrated in FIG. 5, is more comfortable for the patient to wear since there are no wire clasps to impinge on the gum tissue. Further, the preferred functional appliance 38 fits more securely, offers greater stability, and more efficient tooth and supporting alveolar (bone) movement due to the appliances material being vacuum formed to closely conform to the shape of the tooth and the surface mounted undercut. Finally, the functional appliance 38 may be constructed more quickly and at lower cost than an appliance with clasps.

Figure 4:
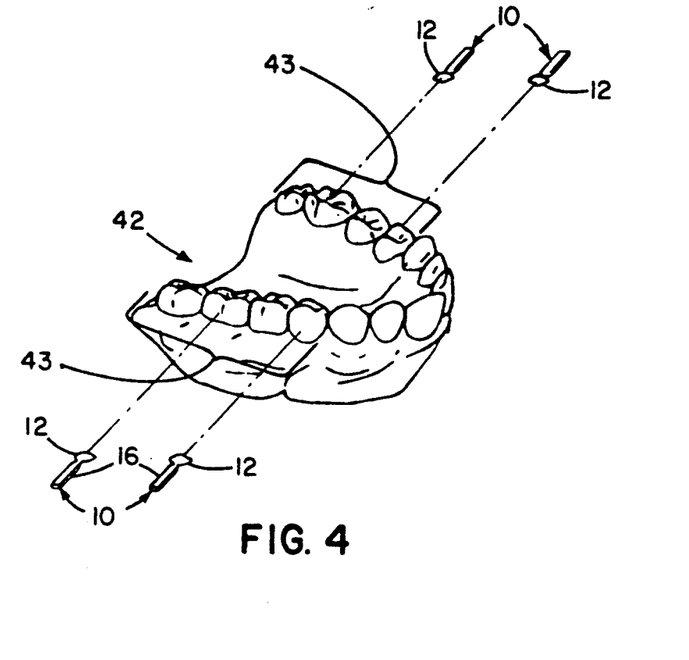
FIG. 4 is a perspective view illustrating the preferred attachment locations of the dental undercuts in the patient's mouth.
Figure 10:
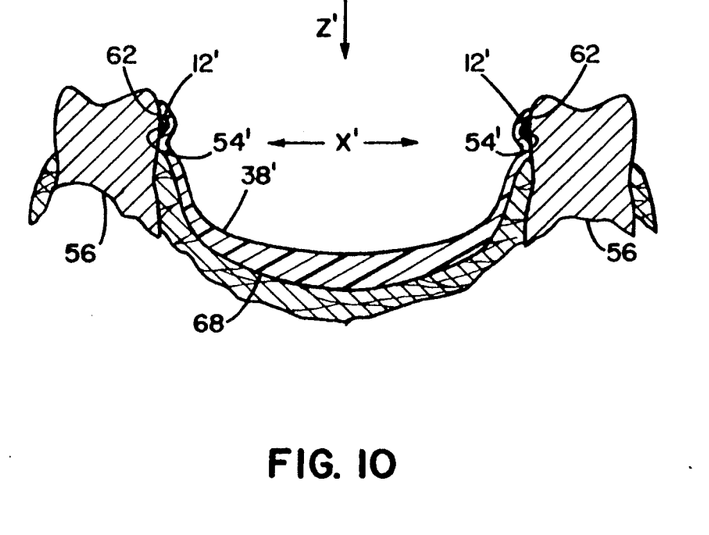
FIG. 10 is a sectional view of the preferred appliance in cooperative engagement with undercuts attached to the lingual (inside) surface of a pair of opposing teeth.

The preferred functional dental appliance 38 of the present invention may be constructed by first attaching at least one of the surface mounted dental undercuts 12 to the outer surface of any tooth, using the procedure and the dental undercut application device 10 discussed above. Preferably, four surface mounted undercuts 12 are placed on each dental arch which will require a dental appliance. FIG. 4 illustrates one possible configuration of the undercuts 12 to the teeth 43 in a particular mouth section 42. For example, the undercuts 12 may be placed on the first molars, the bicuspids, and cuspids or on deciduous molars or deciduous cuspids. FIG. 10, discussed in detail below, illustrates an alternative arrangement where the undercuts 12' are attached to the lingual (inside) surfaces of two or more generally opposing teeth so that the appliance 38 may be pressure fit between the generally opposing teeth and the arch surface in the patient's mouth. It will be understood by those skilled in the art that the surface mounted undercuts 12 may be placed on the teeth where the clasps of a conventional appliance would normally be located, or to any suitable surface required to meet the patient's needs. Further, the undercuts 12 may be relocated during treatment to compensate for movement of the teeth or to provide more secure retention of the appliance.

An impression may then be taken of the patient mouth proximate the surface mounted undercuts. It will be understood that a variety of techniques are available for creating such models, including conventional casting methods or computerized optical scanning. Therefore, the present invention should be understood to encompass forming the dental appliance without creating a model of the patient's mouth.

Depending on the type of appliance required, it may only be necessary to create an impression of a portion of the patient's mouth. For example, a partial denture may only require undercuts adjacent to where the denture will be located. Therefore, the impression may only need to extend over the effected area.

In the preferred embodiment, a shape retaining overlay material (not shown) may be place in the patient's mouth to form an impression of the effected portion of the patient's mouth 42 and the surface mounted undercuts 12. Impression material made of Silica (Amorphous) Diatomite, available from Rockey Mountain Orthodontics of Golden, Colo., is suitable for this purpose. The shape retaining material is removed from the patient's mouth and a casting material is poured into the impression to form a model 44 of the patient's mouth 42 and the undercuts 12, illustrated in FIG. 5. The casting material or dental stone is preferably calcium sulfate alabaster, available from Modern Materials of Cleveland, Ohio. It will be understood by those skilled in that art that a small base 46 (¼ inch high) may be required with a model 44 of the upper arch, whereas a base may not be necessary on the lower arch (not shown).

Attaching the undercuts 12 to the patient's teeth prior to creating the model 44 insures alignment of recesses 54 in the appliance 38 with the undercuts 12 on the patient's teeth, as illustrated in FIG. 5. However, it may be necessary in some situations to create a model of the patient's mouth prior to attaching the undercuts 12, and then attach the undercuts to the model for purposes of forming the dental appliance 38. Next, additional undercuts 12 would then be attached to the patient's teeth proximate to align with the recesses 54 on the appliance 38. It will be appreciated that this procedure may present certain alignment problems. However, it will also be understood that it may be necessary or desirable to move the location of the undercuts 12 during treatment, giving rise to a similar alignment problem. For example, the locations of the undercuts 12 may need to be adjusted to urge the teeth in a particular direction, to compensate for movement of the teeth, or otherwise enhance the operation of the appliance 38.

A sheet of material is then preferably vacuum formed over the model 44, creating the base layer for the preferred appliance 38 which encloses or covers the model of the undercuts 12 and the patient's teeth 43. In the embodiment illustrated in FIG. 5, the engagement surfaces 66 on the appliance 38 are formed to enclose or cover teeth 43 containing undercuts 12. Preferably, the engagement surfaces 66 cover additional teeth not containing undercuts 12, thereby providing additional stability. As will be discussed below in connection with the alternate embodiment illustrated in FIG. 10, the engagement surface 66 need only engage with a portion of the teeth. It will be understood that the appliance 38 may be formed with small engagement surfaces 66, or the engagement surfaces 66 may be trimmed after the vacuum forming step.

Super Clear Splint (0.040") material made from 100% copolyester and sold under the trade name VIVAK, PET-G by Kodak Chemical Products, Inc, of Kingsport, Tenn. is suitable for this purpose. Other materials that would be suitable for this purpose include polycarbinate plastic, P.V.C. plastic, and acrylic plastics.

The vacuum formed sheet of material (i.e., base layer) of the appliance 38 is preferably trimmed after the plastic has cooled and hardened. For a lower arch (not shown), the plastic is preferably trimmed off the model 1½-2 millimeters apically to the gingival crest all the way around the labial, buccal, and lingual surfaces of the model. For an upper arch appliance which includes an expansion joint, as will be discussed in connection with FIG. 6, the plastic may or may not be trimmed to include the upper anterior teeth from cuspid to cuspid, depending on the patient's needs. There is preferably no coverage of the palate. The plastic then covers only the posterior teeth 43 from the first bicuspid distally. If an expansion joint is not used in the appliance, then the plastic may alternatively cover the incisors and posterior teeth. Finally, as discussed above, for embodiments which do not require the engagement surface to enclose the tooth (see FIG. 10), they are simply trimmed to size.

It will be understood that the trimming of the appliance is performed primarily to adjust the size of the engagement surfaces 66, insure a proper fit within a particular patient's mouth and to minimize irritation to the gum tissue. Therefore, the plastic may be trimmed to include all or none of the upper or lower teeth. Trimming the appliance 38 of the present invention is not limited to any particular teeth. Further, it may be possible to form the plastic on the model 44 so that trimming is not required.

An acrylic material may be optionally applied to the vacuum formed base material of the appliance 38, preferably via a "salt and pepper" technique known in the art, using monomer/liquid and polymer/powder. The acrylic material is preferable applied to cover the occlusal, lingual and palate on an upper arch, to add strength and rigidity to the appliance 38. Acrylic may also be applied to any suitable surface for strengthening a lower arch appliance. Acrylic materials made of methyl methacrylate (liquid resin), also know as methyl ester, methacrylic acid, or acrylic resin monomer are suitable for this purpose. Polymethyl methacrylate, methyl methacrylate resin and lucite are suitable powder materials. The acrylic materials discussed above are available from Forestadent of Pforzheim, Germany, under the trade name Forestacryl.

The preferred appliance 38 of the present invention is designed to be semi-rigid and resilient. The preferred materials used to construct the dental appliance 38, such as the acrylic layer, creates a semi-rigid structure that is sufficiently durable to withstand the forces encountered in a patient's mouth. The resiliency or elasticity of the base material enables the engagement surfaces 66 on the appliance 38 to resume their original shape or position after being bent, stretched, or compressed. It will be appreciated that a variety of other materials having these characteristics may be suitable for this purpose.

Figure 9:
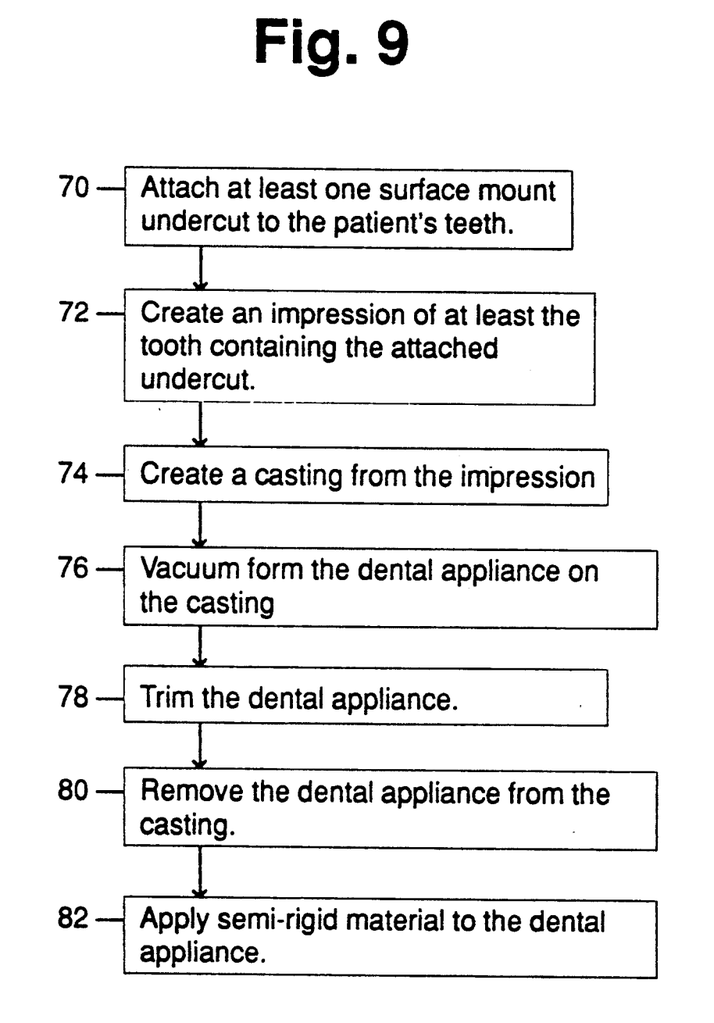
FIG. 9 is a flow chart illustrating the preferred method for constructing the preferred functional dental appliance of the present invention.

By way of summary, the preferred method of constructing the functional dental appliance 38 set forth in FIG. 9 includes; attaching at least one surface mount dental undercut 12 to a tooth in the patient's mouth 70, creating an impression of at least the tooth containing the attached undercut 72, creating a casting from the impression 74, vacuum forming the dental appliance 38 on the casting 76, trimming the dental appliance 38 according to the patient's needs 78, removing the dental appliance 38 from casting 80, and applying an acrylic material to the dental appliance 82.

Figure 6:
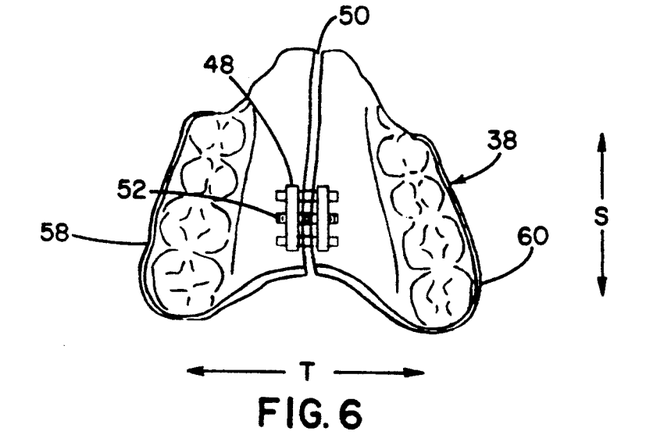
FIG. 6 is an alternate preferred functional appliance incorporating an expansion joint.

In an alternate embodiment shown in FIG. 6, an expansion joint 48 may be place on the base material prior to application of the acrylic. The expansion joint 48 is then preferable encapsulated in the acrylic material. After the acrylic has hardened, a trimming burr is used to create a groove or gap 50 along the axis of the expansion joint 48 so that the relative position of a left half 58 with respect to a right half 60 of the appliance may be adjusted. While expansion joints or screws are generally used in conjunction with transverse or sagittal appliances, use of an expansion joints in the present invention is not limited those appliances. Further, dental appliances 38 constructed according to the technique of the present invention can perform the function of a sagittal or transverse appliance without the use of an expansion joint 48.

The expansion joint 48 is preferably operated by rotating a screw 52 in the center of the joint 48. It will be understood that the operation of the particular expansion joint is not a limitation of the present invention. Further, a variety of expansion joints or other adjustment mechanisms may be incorporated into the dental appliance 38 without departing from the scope of the present invention.

The expansion joint 48 discussed above is particularly suited for increasing or decreasing the transverse pressure "T" applied to the mouth section 42. As will be understood by those skilled in the art, the expansion joint 48 may be oriented to provide variable pressure in the sagittal "S" direction of the patient's mouth. As will be discussed below, adjusting the relative position of the left half 58 and right half 60 of the appliance 38 may also be useful for enhancing the attachment of the appliance 38 to the patient's mouth 42.

FIG. 5 also illustrate the cooperation of the undercuts 12 with recesses 54 formed in the appliance 38 as the engagement surfaces 66 cooperatively engage with teeth in the patient's mouth. As will be understood by the dashed-lines, the recesses 54 on the dental appliance 38 are aligned with the undercuts 12 in the patient's mouth, and the appliance 38 is pressed or snap-fit into engagement with the undercuts 12.

Figure 7:
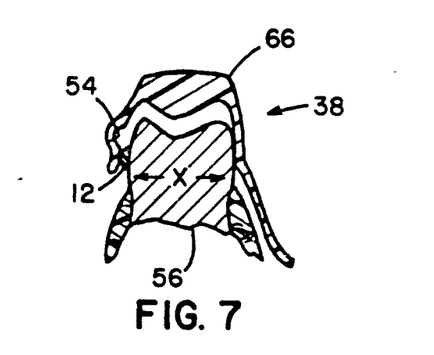
FIG. 7 is a sectional view of the preferred appliance prior to being engaged with a tooth and a surface mounted undercut.
Figure 8:
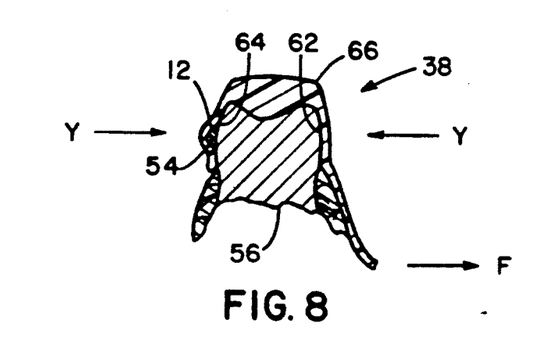
FIG. 8 is a sectional view of the preferred appliance in cooperative engagement with the surface mounted undercut and the tooth.

FIGS. 7 and 8 illustrates a cross section of a representative tooth 56 and the attached surface mounted undercut 12. In FIG. 7, the semi-rigid, resilient appliance 38 is elastically deformed a sufficient amount in the direction "X" prior to engagement with the undercut 12 and the tooth 56.

In FIG. 8, the resilient appliance 38 has returned to its undeformed state, whereby the engagement surfaces 66 enclose or wrap-around the tooth 56. Preferable, the engagement surfaces 66 of the appliance 38 envelop or cover all accessible outer surfaces of the tooth 43, as illustrated in FIG. 5. The semi-rigid nature of the appliance 38 causes the recess 54 to cooperatively engaged with the undercut 12. The engagement surfaces 66 form a pressure fit around the opposing inside surface 62 and outside surface 64 of the tooth 56 in the direction "Y". Further, since the engagement surfaces 66 of the appliance 38 so closely matches the outer surface of the tooth 56 and the undercut 12, a partial vacuum may formed therebetween, further securing the appliance 38.

The cooperative engagement of the semi-rigid, resilient appliance 38 in the direction "Y" may be enhanced by attaching an undercut 12 to the inside surface 62 of the tooth 56 (See FIG. 10). Optionally, the expansion joint 48 discussed in connection with FIG. 6, or some other suitable mechanism may be adjusted to create a force in the direction "F" to enhance the engagement of the recess 54 with the undercut 12, thereby improving the retention capabilities of the appliance 38.

In yet another embodiment, a pair of undercuts 12' are attached to the inside surface 62 (lingual surface) of at least two generally opposing teeth 56, as illustrated in FIG. 10. In this embodiment, the dental appliance 38' does not require engagement surfaces 66 to cover the top surfaces of the teeth 56. This embodiment is desirable so that the engagement surfaces 66 do not interfere with the grinding or cutting surfaces of the patient's teeth. It will be understood that the embodiment discussed in connection with FIG. 10 may be constructed for used in either the upper or lower arch. When used for the lower arch, the embodiment of FIG. 10 is preferably "U" shaped to circumvent the patient's tongue.

In particular, semi-rigid resilient appliance 38' simultaneously presses outwardly in the direction "X'" against the inside surface 62 of the teeth 56 and undercuts 12', and downwardly in the direction "Z" against the arch surface 68. The undercuts 12' engage with the recesses 54' on the appliance 38' to releasably retain the appliance 38' against the arch surface 68 in a pressure-fit engagement relationship.

By utilizing the proper combination and location of undercuts 12 or 12', a variety of functional dental appliances 38 may be releasably secured to a patient's mouth, without the use of wire clasps. Including, but not limited to; binators, Clark twin blocks, sagittal appliances, transverse appliances, bio-finishers, Hawley retainers, T.M.J. splints, and full and partial dentures may be constructed and attached using the method of the present invention.

The present invention is not limited to the examples discussed above, but may be changed or modified without departing from the spirit or scope of the invention. For example, the appliance may be constructed from a variety of materials. It may also be desirable in some circumstances for the undercut to be a variety of shapes which may be more suited to retaining the dental appliances.

What is claimed is:

1. A functional dental appliance system for use within a patient's mouth, the mouth containing at least one tooth having an outer surface, the outer surface of the tooth having a contour, said dental appliance system comprising:
   at least one surface mounted undercut having a back side and a front side, said front side for attachment to the outer surface of the tooth, wherein said back side of said undercut extends outwardly from the outer surface of the tooth when attached thereto, and said back side having a contour generally similar to the contour of the tooth; and
   a dental appliance constructed of a semi-rigid resilient material which generally retains its shape, said appliance including engagement means for engaging said surface mounted undercut when said undercut is attached to the outer surface of the tooth, wherein said means for engaging includes a generally rigid engagement surface having a shape generally conforming with a portion of the contour of the tooth and the outward extension of said attached undercut proximate thereto, said semi-rigid resilient material having sufficient elasticity to permit a first portion of said dental appliance proximate to said engagement surface to move with respect to a second portion of said dental appliance such that said dental appliance flexes prior to engagement with the tooth and said attached undercut, and said dental appliance can be slightly deformed and then return to an undeformed state when engaged with the tooth and said attached undercut in a pressure fit engagement relationship.

2. The functional dental appliance system of claim 1 wherein the patient's mouth includes a plurality of surface mounted undercuts for attaching to a plurality of teeth, said dental appliance having a shape generally conforming with a portion of the contour of the plurality of teeth and said plurality of attached undercuts.

3. The functional dental appliance system of claim 2 wherein plurality of surface mounted undercuts are for attaching to the lingual surfaces of the plurality of teeth.

4. The functional dental appliance system of claim 2 wherein at least two of said plurality of undercuts are for attaching to the lingual surfaces of two generally opposing teeth.

5. The functional dental appliance system of claim 2 wherein four surface mount undercuts are for attaching to a plurality of the patient's teeth.

6. The functional dental appliance system of claim 1 wherein said dental appliance further includes an expansion joint to alter the dimensions of said dental appliance in the transverse direction.

7. The functional dental appliance system of claim 6 wherein said expansion joint alters the dimensions of said dental appliance in the sagittal direction.

8. The functional dental appliance system of claim 1 wherein said dental appliance is a partial bridge.

9. A method for constructing a removable functional dental appliance for insertion into a patient's mouth and for retention within the mouth when engaged with at least one tooth having an outer surface, the outer surface of the tooth having a contour, said method comprising the steps of:
   providing a surface mounted undercut having a back side and a front side for attachment to the tooth;
   attaching said front side of said undercut to the outer surface of the tooth, wherein said back side of said undercut extends outwardly from the outer surface of the tooth when attached thereto, said back side having a contour generally similar to the contour of the tooth; and
   creating a dental appliance constructed of a semi-rigid resilient material which generally retains its shape, said appliance including engagement means for engaging said surface mounted undercut when said undercut is attached to the outer surface of the tooth, wherein said means for engaging includes a generally rigid engagement surface having a shape generally conforming with a portion of the contour of the tooth and the outward extension of said attached undercut proximate thereto, said semi-rigid resilient material having sufficient elasticity to permit a first portion of said dental appliance proximate to said engagement surface to move with respect to a second portion of said dental appliance such that said dental appliance flexes prior to engagement with the tooth and said attached undercut, and said dental appliance can be slightly deformed and then returned to an undeformed state when engaged with the tooth and said attached undercut in a pressure fit engagement relationship.

10. A method of constructing a removable functional dental appliance of claim 9 further including the steps of:
    creating a shape retaining overlay of a portion of the outer surface of the tooth proximate said attached undercut attached such that said overlay retains an impression of the tooth and said attached undercut; and
    creating said dental appliance from said overlay.

11. The method of constructing a removable functional dental appliance of claim 9 further including the steps of:
    creating a shape retaining overlay of a portion of the outer surface of the tooth proximate said attached undercut attached such that said overlay retains an impression of the tooth and said attached undercut;
    pouring a casting material into said impression, creating physical representation of the tooth and said attached undercut; and
    creating said dental appliance from said physical representation.

12. The method of claim 9 wherein said surface mounted undercut is attached to the tooth with an adhesive.

13. The method of constructing a removable functional dental appliance of claim 9 further including the steps of:

defining a three-dimensional representation of a portion of the outer surface of the tooth proximate said attached undercut; and creating said dental appliance from said 3-dimensional representation.

14. A method for constructing a removable functional dental appliance for insertion into a patient's mouth and for retention within the mouth when engaged with at least one tooth having an outer surface, the outer surface of the tooth having a contour, said method comprising the steps of:

providing a surface mounted undercut having a back side and a front side for attachment to the tooth;

creating a shape retaining representation of the outer surface of the tooth proximate the location where said undercut will be attached to the tooth;

attaching said front side of said undercut to the outer surface of said representation of the tooth, wherein said back side of said undercut extends outwardly from the outer surface of said representation of the tooth when attached thereto, said back side having a contour generally similar to the contour of the tooth;

creating a dental appliance constructed of a semi-rigid resilient material which generally retains its shape, said appliance including engagement means for engaging said undercuts attached to said representation of the tooth, wherein said means for engaging includes a generally rigid engagement surface having a shape generally conforming with a portion of the contour of the representation of the tooth and the outward extension of said attached undercut proximate thereto, said semi-rigid resilient material having sufficient elasticity to permit a first portion of said dental appliance proximate to said engagement surface to move with respect to a second portion of said dental appliance such that said dental appliance flexes prior to engagement with said representation of the tooth and said attached undercut, and said dental appliance can be slightly deformed and then returned to an undeformed state when engaged with said representation of the tooth and said attached undercut in a pressure fit engagement relationship; and attaching said front side of said undercut to the outer surface of the tooth in the patient's mouth proximate to the location said undercut was attached to the representation of the tooth on said overlay.

15. A method of removably securing a functional dental appliance within a patient's mouth, the mouth containing at least one tooth having an outer surface, the outer surface of the tooth having a contour, said method comprising the step of:

providing at least one surface mounted undercut attached to the outer surface of the tooth, wherein said undercut extends outwardly from the surface of the tooth, the undercut having a contour generally similar to the contour of the tooth;

providing a dental appliance constructed of a semi-rigid resilient material which generally retains its shape, said appliance including engagement means for engaging said attached surface mounted undercut, wherein said means for engaging includes a generally rigid engagement surface having a shape generally conforming with a portion of the contour of the tooth and the outward extension of said attached undercut proximate thereto, said semi-rigid resilient material having sufficient elasticity to permit a first portion of said dental appliance proximate to said engagement surface to move with respect to a second portion of said dental appliance such that said dental appliance flexes prior to engagement with the tooth and said attached undercut, and said dental appliance can be slightly deformed and then returned to an undeformed state when engaged with the tooth and said attached undercut in a pressure fit engagement relationship; and attaching said dental appliance to said attached undercuts by pressing said appliance in the patient's mouth, causing said engagement surfaces to engage with a portion of the tooth and said undercut.

16. A system for constructing a functional dental appliance system for use within a patient's mouth, the mouth containing at least one tooth having an outer surface, the outer surface of the tooth having a contour, said system comprising an undercut application device including an undercut having a back side, a curved front side for attachment to the outer surface of the tooth, and a removable tab attachment portion interconnected with said back side, said back side having a contour generally similar to the contour of the tooth, the undercut application device further including removable locator tab means interconnected to said removable tab attachment portion for positioning the undercut on the tooth.

17. The system of claim 16 further including a semi-rigid resilient material formable into the dental appliance.

18. The system of claim 17 wherein the resilient material is formable by a vacuum forming process.

19. The system of claim 17 wherein the resilient material is an acrylic plastic.

20. The system of claim 17 further including a quantity of strengthening material for attachment to the resilient material.

21. The system of claim 20 wherein the strengthening material is acrylic.

22. The system of claim 16 further including a quantity of shape retaining overlay material for forming an impression of the patient's mouth.

* * * * *